United States Patent [19]

Grossan

[11] 4,206,756
[45] Jun. 10, 1980

[54] JET EAR IRRIGATION SYSTEM

[76] Inventor: Murray Grossan, 8930 Sepulveda Blvd. S., Los Angeles, Calif. 90045

[21] Appl. No.: 924,192

[22] Filed: Jul. 13, 1978

Related U.S. Application Data

[63] Continuation-in-part of Ser. No. 780,506, Mar. 23, 1977, abandoned.

[51] Int. Cl.$^2$ .............................................. A61M 3/00
[52] U.S. Cl. ..................................... 128/229; 128/239
[58] Field of Search .................. 128/66, 229, 239, 65, 128/67, 24 R

[56] References Cited

U.S. PATENT DOCUMENTS

| 706,602 | 8/1902 | Shaffer | 128/239 X |
| 1,638,532 | 8/1927 | Kallmeyer | 128/239 |

FOREIGN PATENT DOCUMENTS 1158 of 1901 United Kingdom ...................... 128/239

Primary Examiner—John D. Yasko
Attorney, Agent, or Firm—William W. Glenny

[57] ABSTRACT

A system for ear irrigation, consisting of an applicator for applying a solution of water at a temperature of 100° F. to 105° F., and at a pressure pulsating between 0 and 75 psi, at a frequency substantially above 100 cycles per minute—preferably 1,000 cycles per minute or somewhat higher.

The flow of liquid is supplied to the ear by means of an applicator having a tapered end, which ends in a smooth convex manner. The tube connects by a male connector to a standard female counterpart, using a pulsating dental irrigation device. The distal end inserts into the ear, and has a smooth convex ending. At the distal end, three holes are present with accompanying three grooves. The position of the three openings provides for a pulsating solution to eject through two holes on one side and one hole on the opposite side. Thus, the solution rocks the cerumen, pulses the cerumen, and washes it. Yet, it does not strike or injure the eardrum.

Rocking the cerumen, as well as pulsing it, serves to enhance easy removal of the cerumen. This is in addition to the regular washing that the water performs.

Because the openings on the right and left offset each other as the fluid ejects, the distal end of the irrigator vibrates little. At the proximal end, the irrigator tip has three elevations which correspond to the three openings. Thus, the operator can identify the circular position of the three openings without viewing them by observing the three elevations. The tip is provided with a finger grip for grasping and holding the tip effectively. This type of connector allows for swiveling or rotating the ear irrigator tip.

Three channels are cut into the distal end to allow easy access of water and to prevent build-up of water pressure.

5 Claims, 9 Drawing Figures

U.S. Patent Jun. 10, 1980 Sheet 1 of 2 4,206,756
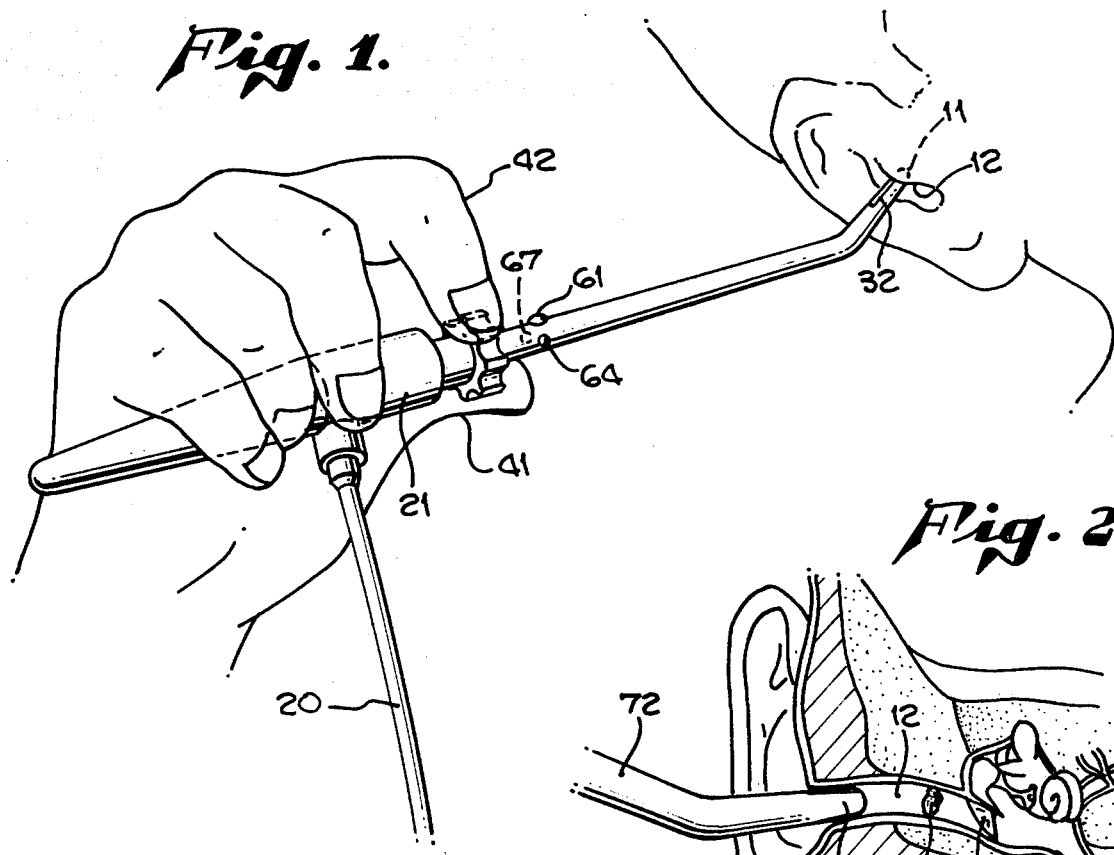
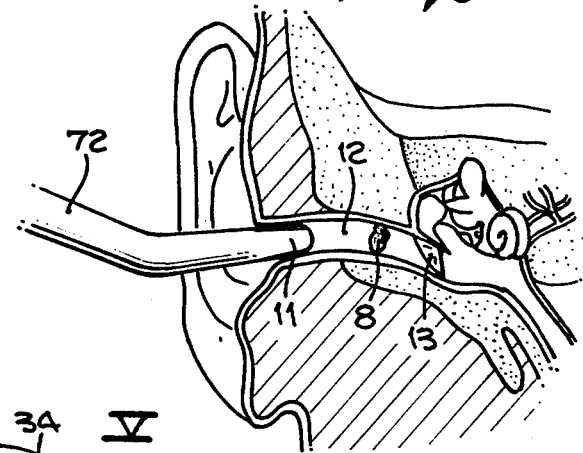
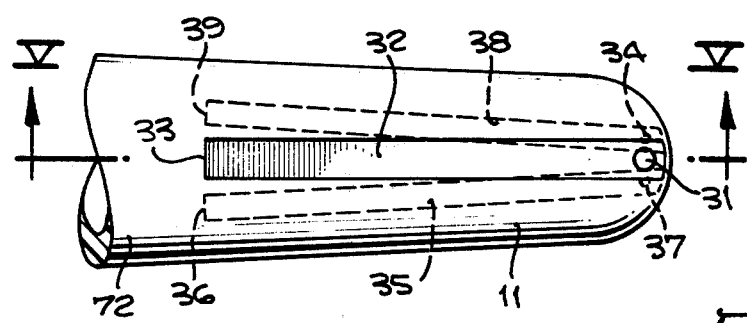
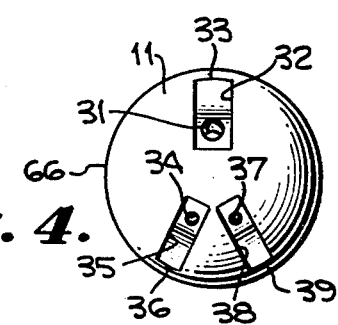
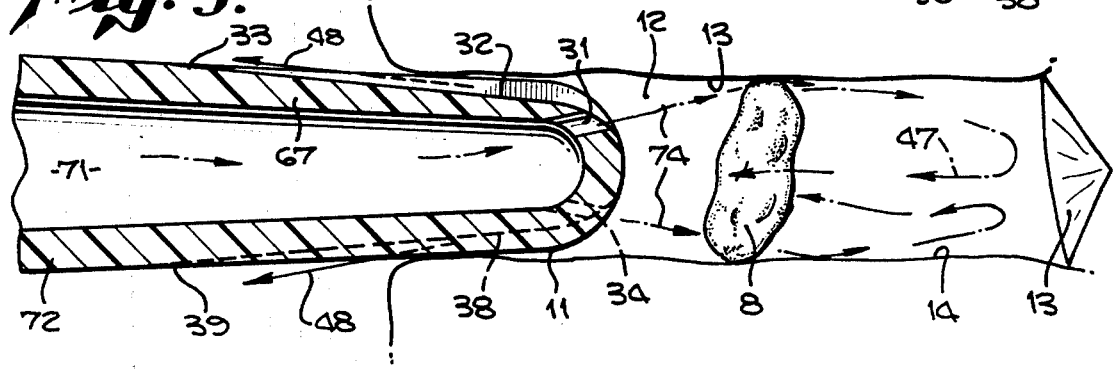

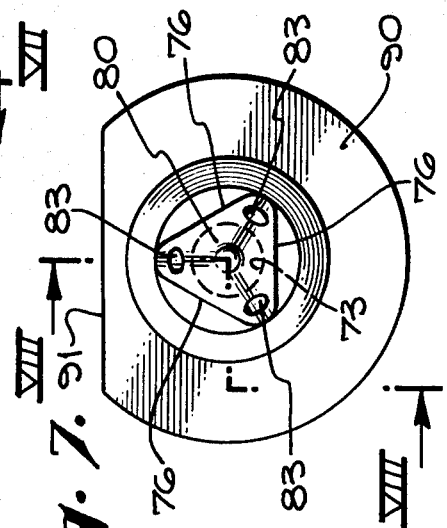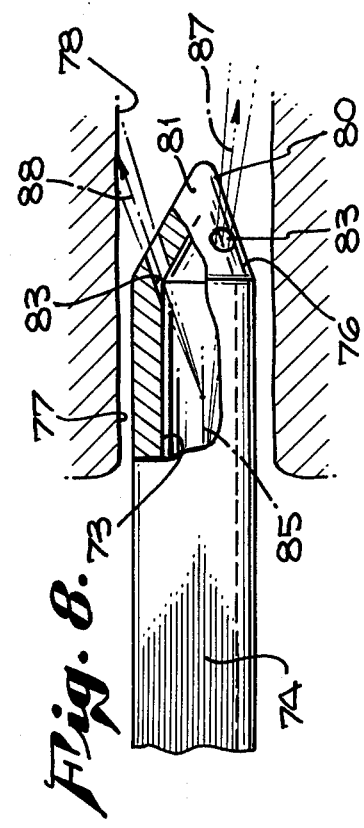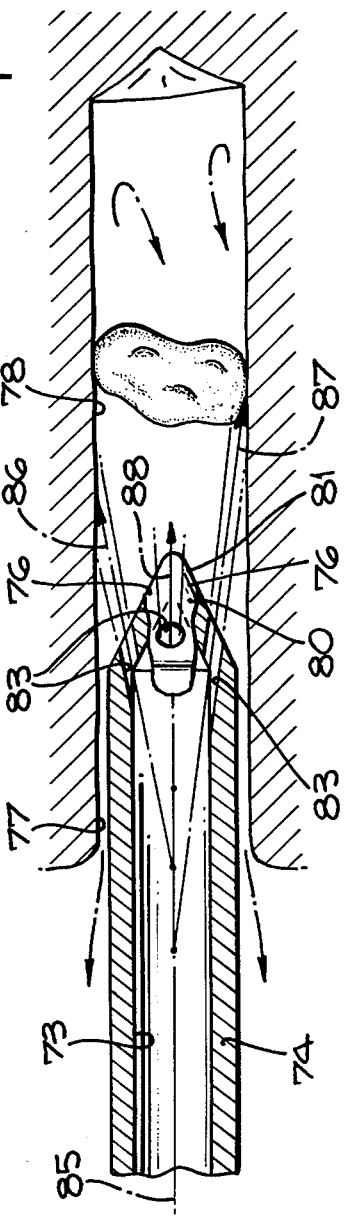

JET EAR IRRIGATION SYSTEM

This application is a continuation-in-part application of copending application Ser. No. 780,506 filed Mar. 23, 1977 now abandoned.

BACKGROUND AND FIELD OF THE INVENTION

It is known that irrigation of the ear with a warm solution is beneficial to removing cerumen (ear wax) as well as foreign material from the ear canal. Both of these frequently occur in the outer ear canal passageway.

The presence of cerumen and other materials may block the normal passage of sound. The present invention is an improvement over prior techniques for irrigation of the ear canal. It contemplates the application to a patient's ear of a pulsating flow of warm water at a temperature of 100° F., or slightly higher. The pressure of the water can be adjusted to pulsate between a pressure of 0 psi and 25 psi, to between 0 psi and 75 psi, at a frequency substantially above 100 cycles per minute—preferably in the order of 1,000 cycles per minute or more.

The solution is applied to the ear canal by means of an applicator having a tubular body, including an elongated tube portion at least several inches long. The proximal end attaches to a handpiece, having a passageway connected to a source of pulsating water solution by means of a male connector. A simple valve on the handpiece allows the operator to turn the water on and adjust the amount of water that goes to the ear irrigator tip.

The distal end of the tube and the end that is introduced into the ear are modified from a standard tubing in the following manner:

1. The end is sealed with a smooth, convex portion presenting towards the eardrum. In the event that the patient accidentally moves and strikes the end of the ear irrigator, the convex smooth end presents an area least likely to produce injury to the eardrum or the canal.

2. Three openings are made into the closed tubing. These openings exit from the sides of the tubing at an angle between 10° and 30° from the length of the tubing. Two openings are made on the left side of the tubing, and one operning is on the right side of the tubing. The diameter of these openings may vary, except that the sum of the two openings on the left side is equal to the diameter of the opening on the right side.

3. Above and external to these openings, grooves are cut which lead to the area of the holes. By having three lateral grooves, a three-part escape mechanism is provided in the event that the irrigator seals within the ear canal. By providing these three exit means, the force of the water pressure cannot be raised between the ear irrigator and the drum.

4. The end of the ear irrigator device is truncated. Therefore, in most situations, the ear canal will be much larger than the end which is introduced into the ear canal.

5. Three elevations are located near the proximal end. These correspond to the three openings to indicate their location when the openings are within the ear canal.

6. The ear irrigator attaches by a male connector to a pump irrigator, female counterpart. This connector allows for free rotation of the distal end.

7. A finger grip is provided for better holding and control of the tip.

8. The tip has several shapes:
A. Straight.
B. Distal end angled at 30°.
C. Distal end angled 60°.
D. Other shapes to suit the physician's uses.

9. The longitudinal position of the three exit holes, from which the water ejects, may vary in relation to each other as in relation to the distal end. This is for the purpose of obtaining a greater degree of rocking of the cerumen, or a lesser degree of rocking of the cerumen—as is desired by the operator. When the holes are located at the same level, there is a slightly lesser degree of rocking; when the large hole is positioned below the level, or proximal to the level of the two smaller holes, a greater degree of rocking is achieved. This is because the water jets strike at different time elements, achieving greater rocking action. Various combinations will be available for varying uses.

Current means of ear irrigation include a large syringe with a large tip. This syringe is alternately filled with water and the syringe forces a stream at large pressure into the ear. No cerumen may be removed if the cerumen is water insoluble. The operator has little or no control over the force of the water being ejected; he cannot see the stream, and the tip often clogs the ear canal and raises pressure very high, and may at times rupture the eardrum.

Or, a pulsating stream my be directed straight forward against the cerumen and eardrum, pulsing at 1,200 pulses per minute. The force striking the eardrum could injure the eardrum, and might cause a rupture. The water pulsing at 1,000 pulses per minute, or greater, would cause the eardrum to vibrate at this rate, thereby causing unusual movement of the eardrum and the three ossicles—maleus, incus and stapes—attached thereby. This forceful movement of the stapes bone within the middle and inner ear is known to be potentially dangerous, and may cause damage to hearing. Because the stream jets forwardly, the distal end of the irrigator vibrates excessively causing abrasion and injury of the ear canal as the end piece moves about irregularly in a circular manner. In addition, the hand piece also vibrates and moves, making it difficult to direct the stream in a desired manner. The water striking straight forward, may strike directly backwards, striking the operator's eye.

Therefore, it is the purpose of this invention to provide a means of utilizing the advantages of pulsing jet stream with the safety of a stream directed in such a manner that it cannot strike the eardrum. In addition to the washing action of the water, the rocking action provides a means of removal of cerumen which is water insoluble. The pulsing action, in addition, helps to remove cerumen. The pulsation and movement of the distal end is reduced by the three jet-opening action. The angle of ejection is such that the water does not strike back in the operator's eye.

The danger of increasing water pressure excessively is prevented by this method because of the three escape grooves, and because the force of the pressure is controlled by means of the pulsating jet source. The source of pulsating flow of water, in accordance with the invention, is most conveniently provided by the conventional device presently being marketed for dental hygiene using a pulsating jet of water, or desired solutions for cleaning the teeth and invigorating the gums. A particular model is provided, such that when the tip is attached the handpiece provides a comfortable, convenient hand grip for the operator, with its own on/off switch to provide one-hand operation with maximum control.

BRIEF DESCRIPTION OF THE DRAWINGS

FIG. 1 is a side view showing the ear irrigator in use. The physician holds the ear irrigator in accordance with this invention, inserted into the patient's ear.

FIG. 2 is an enlarged sectional view of the ear of the patient shown in FIG. 1, with the irrigator tip inserted into the ear canal. The tip is positioned for irrigating wax, or cerumen, from the ear canal.

FIG. 3 is a plan view, partially in section, of the ear irrigator.

FIG. 4 is an enlarged section of an end view.

FIG. 5 is a sectional view taken through V of FIG. 3. The direction of fluid flow is diagrammed.

FIG. 6 is a side elevational view of different embodiment of my invention.

FIG. 7 is an end view taken from the plane indicated by line VII—VII of FIG. 6.

FIG. 8 is an enlarged fragmentary view, partly in section, taken in the plane indicated by line VIII—VIII of FIG. 7 and also showing insertion into an ear canal.

FIG. 9 is an enlarged sectional view of the end portion of the irrigator shown in FIG. 5, partially inserted in an ear canal, and showing dispersion of liquid in the canal by longitudinal spacing of axes of orifices in the end portion of the irrigator.

DETAILED DESCRIPTION

In FIG. 1 there is indicated generally at 10 a patient who is having his ear irrigated by means of this invention. The hand, indicated by 42 for finger, and by 41 for thumb, holds the standard handpiece which is connected by 20 to a typical dental pulsating source of water. Not shown on the handpiece 21 is a simple on/off valve for controlling the amount of water. The water courses through the handpiece 21 through the tube, and exits within the patient's ear at 12. The thumb and forefinger, 41 and 42, grasp the finger grip attached at the proximal end in order to hold the ear irrigator well. Elevations 61, 64 and 67 indicated the location of three openings, now located within the ear canal. The source of liquid under pulsating pressure may be provided by a device of the type exemplified by that shown in U.S. Pat. No. 3,227,158.

FIG. 2 shows the tubular connector 72 ending in a convex smooth portion 11 situated in the correct position within the ear canal 12. 8 indicates a typical particle of cerumen blocking hearing because it blocks the passage of sound to the eardrum 13. The eardrum 13 and the organs directly behind it are delicate, and it is desirable to be extremely gentle in order not to cause damage. The eardrum 13 is very thin and is very fragile, and can be damaged if excessive force or excessive instrumentation is used. FIG. 2 demonstrates that it is not necessary to insert the tip end 11 any further than slightly within the ear canal.

In FIG. 3 greater detail is given to the end of the ear irrigator tip. The tip is truncated so that the diameter reduces as it approaches the end. 72 indicates the hollow channel for the means of bringing liquid to the patient's ear. 39, 33 and 36 indicate grooves cut from the outer surface of the device, thereby allowing for easy egress of any water once within the ear canal. 35, 32, 38 indicate the lateral grooves as they approach the openings and continue onto the position of the openings. 31 is shown in detail as the larger hole, located at the upper end. Indicated are holes 34 and 37 on opposite sides. The lateral grooves 32, 33 are cut so as to provide a means of exit and a channel above the area of the hole 31. The two other channels, 35 and 36, and channel 38-39 are indicated as being on opposite sides of this tubular end.

FIG. 4 is a diagramatic front view illustrating the position of the three ostea. FIG. 4 indicates that the large hole, indicated by 31, is equal in diameter to the sum of the two small holes, 34 and 37. Also indicated are the three exit channels, 32-33 on one side and 35-36 and 38-39 on the opposite side. In FIG. 4 the three openings are indicated as being at the same level. In actual practice, the level of opening 31 will vary, being at the same level as openings 34-37, or inferior to them, in order to achieve better rocking action.

FIG. 5 illustrates in detail the position of the ear irrigator tip within the ear canal. It indicates the solution 71 coursing through the hollow tube and exiting at openings 31 and 34. Not indicated is the simultaneous exiting of the liquid from opening 37. Also indicated is the stream of liquid which strikes unequally at the ear canal 14 and at the cerumen 8. Because the stream strikes at a frequency of approximately 1,000 pulses per minute, it is obvious that this alternate increase and decrease in pressure will wash cerumen and dirt from the ear canal as well as rock it out. Also indicated is the action of the water as it courses within the ear canal 14. Notice that the direct jet stream does not strike the eardrum 13. Indicated in this illustration is a situation in which the ear irrigator tip fills the ear canal. This is an uncommon situation because usually the diameter of the truncated end of the irrigator tip will be considerably less than the diameter of the ear canal. For safety purposes, however, the lateral grooves 32-33, 38-39 which provide a means of exit of water in the event that the ear canal diameter is very small. Not illustrated in this picture, but indicated, is the lateral groove exit means of 35-36. It will be obvious that because the jet streams exit at the angle and manner shown, and because the sum of the diameter of opening 31 is equal to the sums of the diameters 34 and 37, that the tip end 11 vibrates very little because the direction of the streams is away from each other, thus reducing vibration of the end of the tip.

As the liquid dissolves the cerumen, the cerumen may exit either through the ear canal directly by pressure of liquid which is also exiting, or through the channels of exit provided, as indicated by 32-33, 35-36 and 38-39. Accordingly, there is provided an ear irrigation system using an irrigator applicator of specific design to be used in connection with a source of solution pulsating at a rate of about 1,000 cycles per minute or more, with a pressure of approximately 0.75 psi.

In FIGS. 6-9, inclusive, a different embodiment of the invention is shown and comprises a hollow tubular cylindrical body 70 having a longitudinal axis and provided at one end 71 with a suitable fitting 72 for a releasable connection to a handle such as 21 of the prior embodiment. Hollow body 70 provides an axial passageway 73 for liquid entering at 72 and for discharge through end portion 74. End portion 74 is of reduced outer diameter and may join body 70 through a tapered intermediate portion 75. End portion 74 is provided with three flat sides 76 providing a generally triangular cross sectional shape whereby each flat side 76 may define with the wall surface 77 of an ear canal an enlarged passageway to facilitate outflow of liquid from the ear canal 78.

End portion 74 has an end tip 80 of generally conical shape and which provides an end wall section 81 disposed transversely of the axis of body 70 for preventing direct coaxial discharge of liquid from end portion 74. End tip 80 is provided with two or more liquid discharge orifices 83. In this example, three discharge orifices 83 are shown, each being formed in tip 80 at the thicker metal section provided between the included angles formed by flats 76 on tip portion 74. As in the prior example of this invention, orifices 83 may be of the same diameter or one of the orifices 83 may be of a larger diameter to provide a larger flow area for discharged liquid. It is important to note in this example of the invention that, as shown in FIG. 9, the axis of each orifice intersects the axis 85 of the tubular body at points spaced from one another. In other words, axis 86 of the upper orifice 83 intersects axis 85 downstream from the intersection of axis 87 of the lower orifice 83 as shown in FIG. 9. Axis 88 of the other orifice intersects axis 85 at a point spaced downstream from axis 86. It should be noted that in the showing of the intersecting axis in FIG. 9 that the tubular member has been turned 90° from its position in FIG. 7 in order to better illustrate the spaced intersections of the axes of the orifices 83 with axis 85 of the tubular member. As further illustrated by phantom lines in FIG. 9, the spacing of such intersections of axes causes the streams of liquid discharged from orifices 83 to strike the wall surfaces 77 of the ear canal at axially displaced areas as well as circumferentially spaced areas on the inner wall surface 77. Thus, substantial dispersions of the liquid streams are produced so that harmful direct impingement of a coaxial stream of liquid against the eardrum is avoided. Further, such dispersion and displacement of areas of contact of the liquid streams on the surface of the ear canal facilitates the dislodgement of cerumen. The selected angle of dispersion avoids having the water strike back into the operator's eye. The location of orifices 83 and a selected top orifice, FIG. 7, is facilitated by a collar 90 having a flat face 91. Collar 90 may be secured to body 70 in any suitable manner and during such securement may be readily oriented with a selected orifice 83 so that the operator will be aware of the orientation of the orifices 83 in the ear canal.

Irrigation of an ear canal with the irrigator of this embodiment is substantially the same as that described above for the prior embodiment of this invention. It is desirable that a pulsating source of liquid is utilized to facilitate the dislodgment of cerumen in the ear canal. The arrangement of the orifices in the end tip portion of body 70 prevent direct impingement of a stream of liquid on an eardrum, prevents or reduces to an insignificant amount vibration of the pulsating liquid from being transmitted to the hand of the operator and also to the wall of the ear canal because of the dispersion of the liquid in the ear canal. This angle of dispersion avoids having the water strike backwards into the operator's eye. This allows the operator to clearly visualize the tip end within the canal, the cerumen and significantly aids in better performance of the irrigation procedure.

Various changes and modifications in the exemplary embodiments of the invention described above may be made within the spirit of this invention and all such changes and modifications coming within the scope of the appended claims are embraced thereby.

I claim:

1. An irrigation device for use in an ear canal having a tympanic membrane thereacross at one end thereof, comprising:
    a tubular cylindrical body having an axis and providing an internal bore along said axis, said body having an end portion of reduced diameter to be inserted into an ear canal,
    said end portion having an end tip with an end wall section lying across said axis and provided with orifice means spaced from said end wall section including orifices having axes which are inclined forwardly and outwardly relative to said body axis, said orifices constituting the only outlet for pressurized liquid in said bore, the inclination of the orifice axes adapting the orifices to direct impingement of said liquid against wall surfaces of said ear canal without direct impingement of an axial stream against said membrane, said end portion having an external configuration adapted to provide outflow passageways for liquid introduced into said ear canal.

2. The invention as defined in claim 1 wherein said end portion is triangular in section and there are three orifices, each disposed adjacent to a vertex of said triangular section.

3. The invention as defined in claim 1 including orienting means on said tubular body in oriented relation with respect to at least one of said orifices.

4. The invention as defined in claim 1 wherein all orifices but one are disposed symmetrically relative to a radial plane including the axis of said one orifice.

5. A device as stated in claim 1 wherein
    the axes of said orifices intersect the axis of the tubular body at longitudinally spaced points therealong whereby liquid discharged from said orifices is adapted to strike wall surfaces of an ear canal and cerumen at axially and circumferentially spaced areas.

* * * * *